United States Patent [19]

Foster

[11] Patent Number: 4,576,097

[45] Date of Patent: Mar. 18, 1986

[54] PIPELINE INSPECTION VEHICLES

[76] Inventor: John L. Foster, 49 Oakland Rd., Monkseaton, Tyne & Wear, England

[21] Appl. No.: 667,392

[22] Filed: Nov. 2, 1984

Related U.S. Application Data

[63] Continuation of Ser. No. 276,889, Jun. 24, 1981, abandoned.

[30] Foreign Application Priority Data

Apr. 27, 1981 [GB] United Kingdom ............... 8112915

[51] Int. Cl.[4] ..................... B61B 13/10; B65G 51/00
[52] U.S. Cl. ................. 104/138 G; 104/155; 105/365; 406/10; 406/190
[58] Field of Search ............... 104/138 R, 138 G, 155; 324/220, 221; 137/345; 251/305; 105/365; 378/60; 250/358.1; 73/40, 40.5 R, 40.5 A; 406/10, 184, 185, 190

[56] References Cited

U.S. PATENT DOCUMENTS

| | | | |
|---|---|---|---|
| 3,036,530 | 5/1962 | Mius et al. | 104/138 G |
| 3,087,439 | 4/1963 | Petrocokino | 104/138 G |
| 3,147,773 | 9/1964 | Matthews et al. | 251/305 X |
| 3,495,546 | 2/1970 | Brown et al. | 104/138 G |
| 3,758,050 | 9/1973 | Watts et al. | 104/138 R X |
| 4,105,972 | 8/1978 | Smith | 324/220 |
| 4,114,835 | 9/1978 | Alexandrov et al. | 104/155 X |
| 4,295,632 | 10/1981 | Engelke | 251/305 X |
| 4,388,871 | 6/1983 | Braithwaite et al. | 104/138 G |

Primary Examiner—Randolph A. Reese
Attorney, Agent, or Firm—Lalos, Keegan, Marsh Bentzen & Kaye

[57] ABSTRACT

A pipeline inspection vehicle has at least one resilient driving cup mounted around the body of the vehicle so as to contact the interior wall of the vehicle and thus provide a pressure differential across the driving cup which will propel the vehicle along the pipeline. An annular array of ducts extends through the body of the vehicle to by-pass fluid through the driving cup, each duct being provided with a control valve for regulating the flow of fluid through the duct. A control arrangement is provided for opening and closing the control valves in dependence on the speed of the vehicle, thereby to adjust the speed of the vehicle in accordance with a desired speed.

6 Claims, 3 Drawing Figures

FIG.2.
FIG.3.
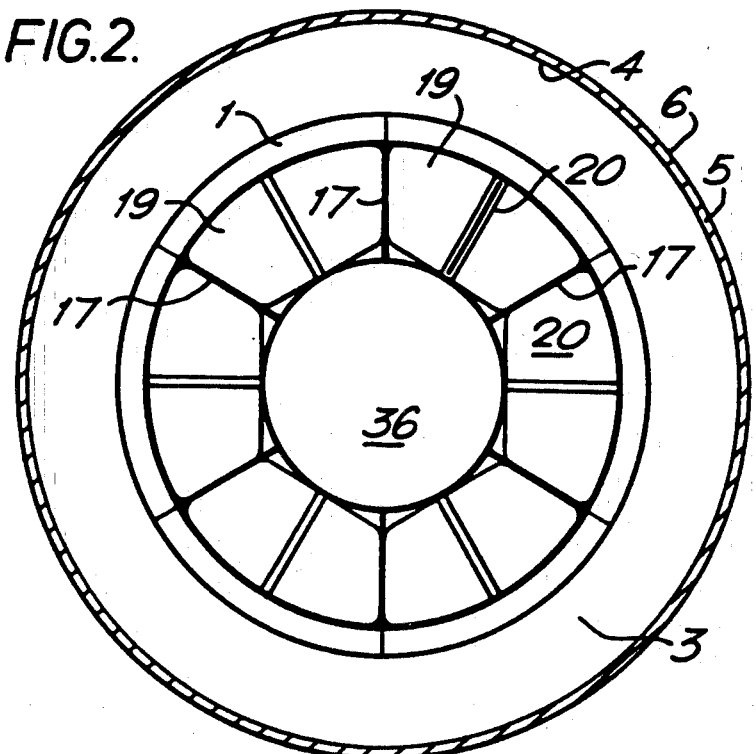
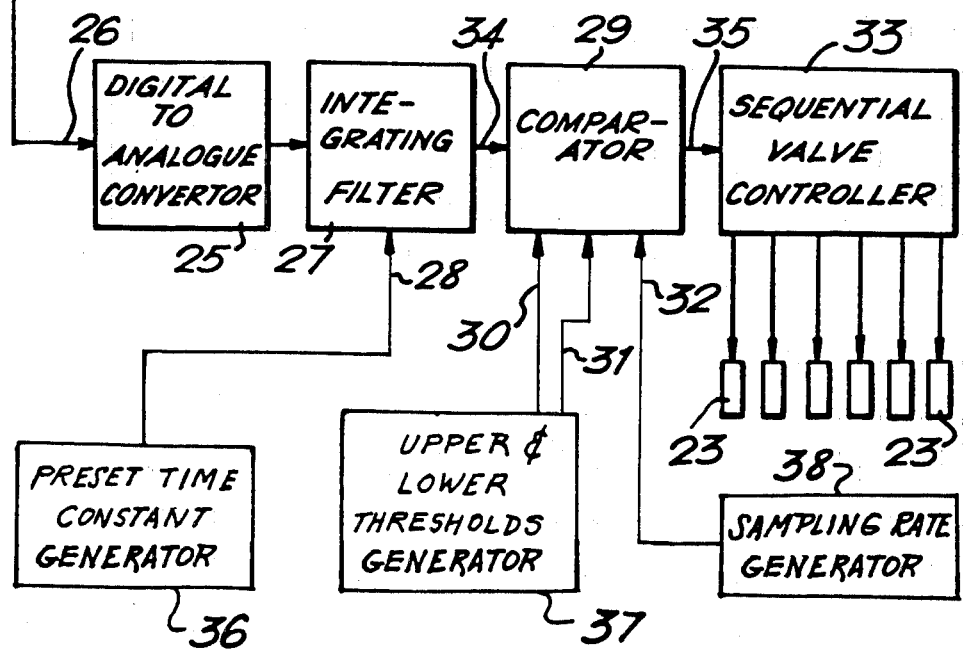

PIPELINE INSPECTION VEHICLES

This application is a continuation of application Ser. No. 276,889, filed June 24, 1981, now abandoned.

This invention relates to a pipeline inspection vehicle of a kind which is propelled along the pipeline by pressure produced by fluid flowing along the pipeline, and to a pipeline inspection system utilizing such a vehicle.

The internal and external surfaces of a pipeline used for conveying fluids, such as liquids or gases, are inspected for surface irregularities or flaws by a vehicle which carries the necessary instrumentation for performing the task and which is propelled along the pipeline by the fluid flowing in the pipeline. To this end, resilient driving cups are mounted around the body of the vehicle so as to contact the interior wall of the pipeline and seal the gap between the body of the vehicle and the pipeline. The flow of fluid along the pipeline creates a differential pressure acting across the resilient driving cups which thus provides the driving force for propelling the vehicle. With such pipeline inspection vehicles it is important that they should be propelled at a reasonable constant speed which is as close as possible to the optimum speed necessary to enable the instruments to carry out a full and accurate inspection. However, variations in the differential pressure can lead to fluctuations of the speed of the vehicle which are often accompanied by high and unacceptable accelerations and decelerations. Such variations in the differential pressure may be caused by bore variations, changes in a wall friction characteristics, or by bends or changes in the inclination of the pipeline.

In addition to controlling fluctuations of speed arising from the above mentioned causes, it may also (or alternatively) be necessary to reduce the average speed of the pipeline vehicle below that of the propelling fluid, where the velocity of the transporting fluid exceeds that at which the inspection vehicle can satisifactorily function.

In U.S. Patent Specification No. 3,495,546 it is proposed to vary the speed of a pipeline inspection vehicle by providing a central bypass valve to allow gas within the pipeline to bypass resilient driving cups and hence control the differential pressure across the cups. The use of a central bypass valve in this way has not proved completely satisfactory as a speed control system for two reasons. In the case of speed fluctuations caused by drag variations and the like, a very fast response control system is required to prevent the pipeline vehicle stopping before the differential pressure control bypass valve operates. Gas bypass valves are not inherently suitable for this type of speed smoothing control because of the long time necessary to create a change in the differential driving pressure acting across the vehicle seals. The most suitable system for this type of control is a braking control system such as that proposed in U.S. Pat. No. 4,388,871 in which selectively operable friction brakes acting against the pipe wall provide a controllable and variable drag to the vehicle to smooth out the vehicles speed. Bypass valves are in principle suitable only for speed reduction systems. In this case, however, to provide a useful speed reduction (relative to the transporting fluid), a large bypass area is required. It is not possible for configuration covered by U.S. Pat. No. 3,495,546 to provide a large enough flow area to be useful in this way.

An object of this invention is to provide an improved pipeline inspection vehicle designed to travel through a pipeline at a speed significantly less than that of the fluid in the pipeline.

According to the present invention a pipeline inspection vehicle comprises at least one resilient driving cup mounted around the body of a vehicle so as to contact the wall of the pipeline and thus provide a pressure differential across the driving cup which will propel the vehicle along the pipeline, an annular array of ducts extending through the body of the vehicle to bypass fluid through the driving cup, each duct being provided with a butterfly valve for regulating the flow of fluid through the duct, and means for opening and closing the butterfly valves in dependence on the speed of the vehicle thereby to adjust the speed of the vehicle in accordance with a desired speed.

An advantage of the pipeline inspection vehicle of this invention is that the annular array of ducts provides a smooth and flexible control of the speed of the vehicle since a relatively large proportion of the cross-sectional area of the vehicle can be utilized for the ducts.

Preferably, the annular array of ducts is disposed around the periphery of the body of the vehicle.

The pipeline inspection vehicle may comprise at least six ducts in juxtaposition around the periphery of the vehicle body.

The butterfly valves in the ducts may be opened and closed in a predetermined sequence in dependence on the speed of the vehicle. The means for opening and closing the butterfly valves in the ducts may include fluid-energized actuators utilizing the fluid pressure differential across the resilient driving cup for actuating the butterfly valves. Preferably, solenoid-operated valves are provided for controlling the supply of this fluid pressure to said actuators. Then the solenoid-operated valves may be operatively controlled by a control circuit arrangement. The control circuit arrangement may comprise means for generating a first signal indicative of the actual speed of the vehicle, means for generating a second signal indicative of a predetermined desired speed, and means for comparing the first and second signals and providing an error signal for controlling the operation of the valves in the ducts to maintain the vehicle at the desired speed.

The control circuit arrangement for operating the valves may be accommodated in a housing located within the annular array of ducts.

The invention also resides in a pipeline inspection system incorporating a pipeline inspection vehicle as defined above.

An embodiment of the invention will now be described, by way of example, with reference to the accompanying schematic drawings in which:

FIG. 2 is a rear view of the pipeline inspection vehicle shown in FIG. 1;

FIG. 3 is a block diagram of a control circuit of the pipeline inspection vehicle shown in FIGS. 1 and 2.

Figure 1:
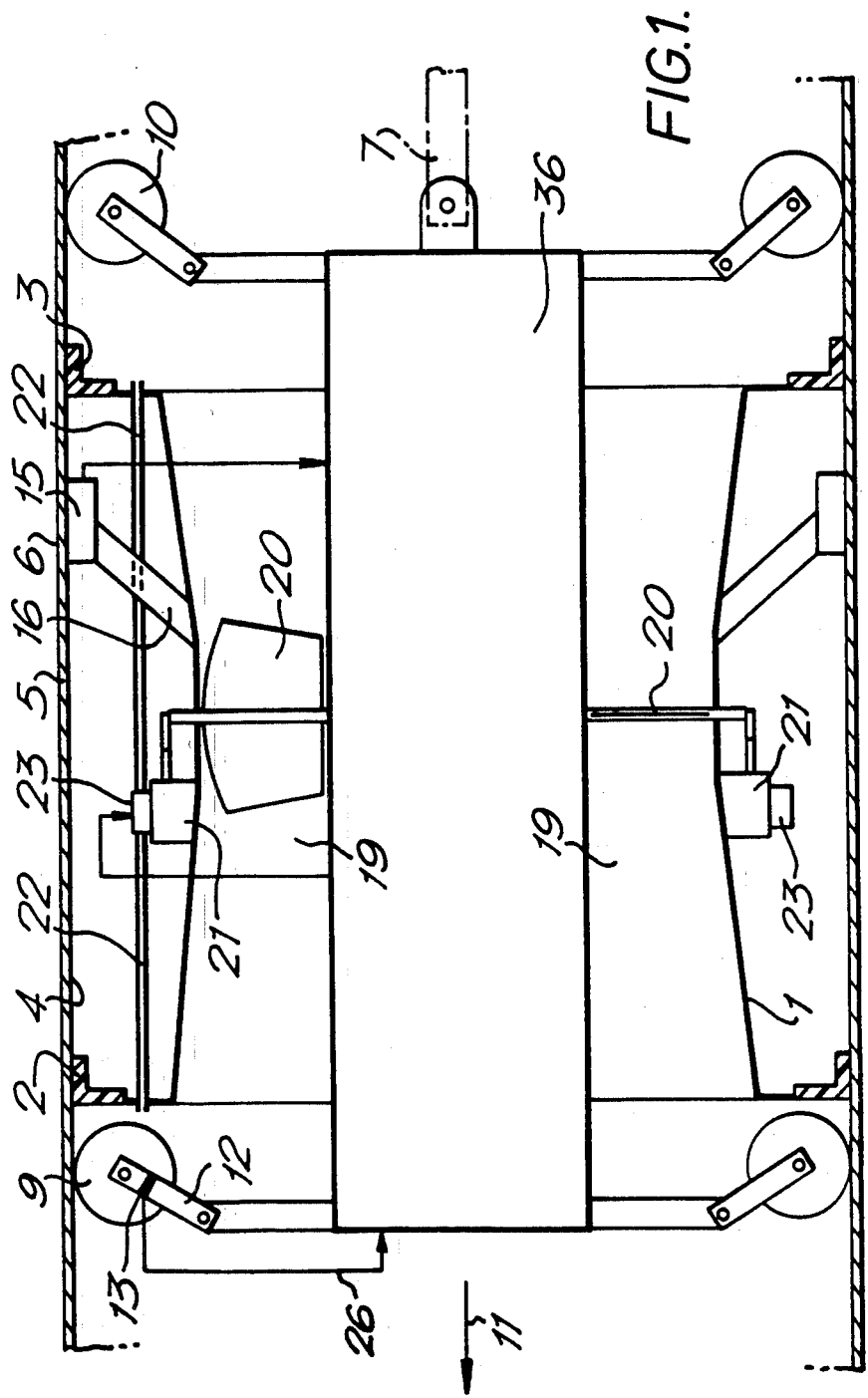
FIG. 1 is a sectional side elevation of a pipeline inspection vehicle in accordance with the invention located within a pipeline.

Referring in the first instance to FIGS. 1 and 2, the pipeline inspection tractor vehicle comprises a main tubular body 1 provided with a front flexible polyurethane driving cup 2 and a rear flexible polyurethane driving cup 3. The flexible driving cups 2 and 3 which are attached to the tubular body 1 are arranged to press against the interior surface 4 of the cylindrical wall 5 of the pipeline 6 along which a fluid such as gas under pressure is being conveyed and thus provide a pressure differential across the cups 2 and 3 which will act to propel the vehicle along the pipeline 6. The tractor vehicle may be coupled to a further towed vehicle (not shown) through a flexible coupling 7. The tractor vehicle is supported on a plurality of wheels 9 at the front of the vehicle body 1 and a like plurality of wheels 10 at the rear of the vehicle body. The wheels 9 and 10 engage the interior surface 4 of the pipeline 6 to permit the vehicle to travel along the pipeline in the direction indicated by the arrow 11. The wheels 9 are mounted on arms 12 which incorporate suitable velocity sensors 13 which generate a digital output signal indicative of the rotational speed of the wheels along the interior of the pipeline.

Also mounted on the tubular body 1 is a pipeline inspection apparatus which detects flaws in the pipeline using a magnetic flux-leakage technique, for example of the kind described in U.S. Pat. No. 4,105,972 in which a plurality of magnetic sensing shoes 15 are supported in close proximity with the interior surface 4 of the pipeline 6 by resilient arms 16. The sensing shoes 15 are arranged to detect changes in magnetic flux caused by disconformities in the pipe wall, the magnetic flux being induced in the wall 5 by magnets (not shown) carried on the vehicle. The tubular body 1 also includes an annular array of six ducts 19 extending between the front driving cup 2 and rear driving cup 3 to by-pass the fluid through the driving cups 2 and 3. The six ducts 19 are arranged in juxtaposition around the periphery of the vehicle body 1 with relatively thin dividing walls 17 between them.

Each of the ducts 19 is provided with an individual butterfly valve 20 arranged to be moved between a position in which it substantially occludes the duct 19 and a position in which the duct provides a substantially free passage for the fluid. The butterfly valves 20 are arranged to be operated by any suitable kind of known fluid-energized actuators 21 which in this case utilize the fluid pressure differential across the resilient driving cups 2 and 3. The fluid under pressure is supplied to the actuators 21 through an acutator supply line 22, the supply of fluid to the actuators being controlled by solenoid operated valves 23. The solenoid operated valves 23 are of the well known latched-impulse type which only require a relatively short electric current pulse to operate them, thus using a minimum of electrical power. Referring now to FIG. 3, the control circuit comprises a digital-to-analog converter 25 which receives the digital input signal from the velocity sensor 13 on an input lead 26 and applies an analog output voltage to an integrating filter 27. A signal indicative of a preset time constant is applied from a suitable signal generator 36 to an input lead 28 of the integrating filter 27 which applies said first output voltage signal indicative of the actual speed of the vehicle by way of output lead 34 to a comparator 29. The comparator 29 is fed with said second signals from a suitable signal generator 37 on input leads 30 and 31 respectively indicative of predetermined upper and lower thresholds of the vehicle speed and is also fed with a further input signal from a suitable signal generator 38 indicative of a preset sampling rate on an input lead 32.

The comparator 29 is arranged to provide a velocity error signal on output lead 35 which is obtained by comparing the actual vehicle speed, as indctated by the first signal on lead 34. With a predetermined target speed range as indicated by the second signals on leads 30 and 31. The error signal is smoothed by a single term integrator with a preset constant incorporated in the comparator 29, and the error signal is sampled at preset intervals determined by the sampling rate signal on input lead 32 and this sampled output is applied to a sequential valve controller 33. The apparatus of the control circuit of FIG. 3 is enclosed in a hermetically sealed compartment 36 located in the tubular body 1 within the annular array of ducts 19.

The valve controller 33 is arranged to actuate the solenoid operated valves 23 in sequence, depending on whether the sampled error signal is above or below the speed range defined by the signals indicative of the threshold values. The solenoid valves 23 operate the butterfly valves 20 in sequence through the intermediary of the fluid-energized semi-rotary actuators 21. Thus, if the sampled velocity is below the lower threshold, then the last butterfly valve 20 to be opened will be closed. Conversely if the sampled velocity is above the upper threshold then the last valve to be closed will be opened. In this way the control circuit provides a smooth and efficient control of the speed of the vehicle based on the upper and lower threshold values. While the pipeline inspection vehicle described above has an annular array of six ducts controlled by butterfly valves it will be appreciated that an annular array comprising a greater or smaller number of ducts could be used. Moreover, while butterfly valves are preferred, since they leave a relatively small proportion of the duct cross-section un-occluded when the valve is in the open position, other forms of control valve may be used in the ducts.

It should also be appreciated that although the embodiment of the invention described above incorporates inspection apparatus which detects flaws magnetically, the inspection apparatus could equally well incorporate elastic wave, i.e. ultrasonic, inspection apparatus.

I claim:

1. A pipeline inspection vehicle which is propelled along the pipeline by pressure produced by fluid flowing along the pipeline and which comprises:
    (a) a vehicle body;
    (b) at least one resilient driving cup mounted around said vehicle body so as to contact the interior wall of the pipeline and thus provide a fluid pressure differential across the driving cup which will propel the vehicle along the pipeline;
    (c) an annular array of ducts disposed around the periphery of said vehicle body and extending through said vehicle body to by-pass fluid through said driving cup;
    (d) a butterfly valve in each said duct for regulating the flow of fluid through said duct; and
    (e) a means operatively connected to said butterfly valves to open and close said butterfly valves in a manner so as to maintain a steady speed of said vehicle body in the pipeline which speed is less than that of the fluid flow in the pipeline.

2. A pipeline inspection vehicle as claimed in claim 1, wherein the annular array of ducts comprises at least six ducts in juxtaposition around the periphery of the vehicle body.

3. A pipeline inspection vehicle as claimed in claim 1 wherein the butterfly valves in the ducts are arranged to be opened and closed by said means in a predetermined sequence in dependence on the speed of the vehicle.

4. A pipeline inspection vehicle as claimed in claim 1, wherein the means for operating the butterfly valves in the ducts includes fluid-energized actuators coupled to said valves and utilizing the fluid pressure differential across the resilient driving cup, and solenoid-operated valves which control said differential fluid pressure supply to said actuators.

5. A pipeline inspection vehicle as claimed in claim 4, wherein the means for opening and closing the butterfly valves in the ducts further includes a control circuit arrangement accommodated in a housing within the annular array of ducts and arranged to actuate said solenoid-operated valves.

6. A pipeline inspection vehicle as claimed in claim 5, wherein the control circuit arrangement comprises means for generating a first signal indicative of the actual speed of the vehicle, means for generating a second signal indicative of a predetermined desired speed, and means for comparing the first and second signals and for providing an error signal for controlling the operation of the butterfly valves in the ducts.

* * * * *